(12) United States Patent
Fujita et al.

(10) Patent No.: US 6,486,095 B1
(45) Date of Patent: Nov. 26, 2002

(54) AGRICULTURAL CHEMICALS FORMULATION FOR RICE PADDY FIELD, PREPARATION THEREOF AND THE METHOD FOR SCATTERING THE SAME

(75) Inventors: Shigeki Fujita, Iwata (JP); Tohru Takayanagi, Morioka (JP); Susumu Kato, Shizuoka (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/940,574

(22) Filed: Aug. 29, 2001

(51) Int. Cl.$^7$ .................................................. A01N 3/02
(52) U.S. Cl. ...................................................... 504/116
(58) Field of Search .................................. 504/367, 116

(56) References Cited

FOREIGN PATENT DOCUMENTS

| | | |
|---|---|---|
| JP | 2000-54259 | 2/2000 |
| JP | 2000-128173 | 5/2000 |

Primary Examiner—Alton N Pryor
(74) Attorney, Agent, or Firm—Oblon, Spivak, McClelland, Maier & Neustadt, P.C.

(57) ABSTRACT

In an agricultural chemicals formulation which is scattered by being thrown directly into a paddy field filled with water, it is an object to provide a composition having an excellent spreadability without stagnation of an agrochemically active ingredient at the point of throwing, and in particular to provide a labor-saving formulation for scattering (application) which contains a liquid agrochemically active ingredient at room temperature, and to provide an agricultural chemicals formulation containing a liquid agrochemically active ingredient at room temperature in high concentrations, which have been difficult to be realized. The agricultural chemicals formulation for a rice paddy field is produced by preparing a granular composition in a manner that a mixture of a liquid agrochemically active ingredient at room temperature, a surfactant, and a substance exhibiting a thickening function or a gelation function in the water, is held and carried by a granular nucleus, and packing it with a water-soluble film. The present invention also provides a method of scattering (applying) the agrochemically active ingredient, which is characterized by that the agricultural chemicals formulation is directly thrown into a paddy field filled with water at a rate of 2 to 20 bags per 10 a.

11 Claims, 1 Drawing Sheet

AGRICULTURAL CHEMICALS FORMULATION FOR RICE PADDY FIELD, PREPARATION THEREOF AND THE METHOD FOR SCATTERING THE SAME

FIELD OF THE INVENTION

The present invention relates to an agricultural chemicals formulation for a rice paddy field, to scatter (apply) directly on the water surface, and more in detail, it relates to an agricultural chemicals formulation for a rice paddy field suitable for the agricultural chemicals being scattered (applied) uniformly by throwing a granular agricultural chemicals composition packed in a bag made of a water-soluble film and the like directly on the water surface of a rice paddy field filled with water, the preparation thereof and the method for scattering (applying) the same.

DESCRIPTION OF RELATED ART

At present, as a major agricultural chemicals formulation, a granulated type, a powder type, emulsifiable type, wettable type, suspension type, granulated hydrate type and so on are known. However, in recent years, saving labor for scattering (applying) agricultural chemicals and cutting down of agricultural chemicals have become important and improvement of the formulation form of the agricultural chemicals is required.

Under these circumstances, recently, labor-saving formulations which can be scattered (applied) only by throwing the agricultural chemicals from a path between rice paddy fields without entering into the rice paddy has been studied. Such a formulation is premised on being scattered in a rice paddy field unevenly, and therefore it has been demanded to develop a formulation whose agrochemically active ingredients float and spread on the water surface to obtain a desirable spreadability of the components.

Various studies have been made for such a demand, but actually no agricultural chemicals formulation has been obtained, which are perfectly satisfactory for agrochemically active ingredients having various properties. For instance, a method to pack emulsion containing an agrochemical insecticide ingredient of a water-soluble film and to throw it into a paddy field filled with water is disclosed (Japanese Patent Publication No. Sho 42-5240). However, the technology disclosed here has a disadvantage that a large quantity of the agricultural chemicals ingredients remain in the soil at the point of throwing after the treatment.

Various technologies have been disclosed, for instance, a formulation in which agrochemically active ingredients are impregnated into a foamed plastic material having particle sizes of 0.1 mm to 10 mm and packed with a water-soluble film (Japanese Patent Laid-open No. Sho 53-99327); an agricultural chemicals formulation for throwing into a paddy field in which water-floatable solid agricultural chemicals containing an agrochemically active ingredient, a water-floatable granular nucleus chosen from calcined vermiculite, foamed pearlite, foamed shirasu, and cork, a surfactant (acetylene alcohol) are packed with a water-soluble film (Japanese Patent Laid-open No. Hei 6-336403); and a formulation in which agrochemically active ingredients of agricultural chemicals are coated on and carried by a granular nucleus such as pumice or calcined pearlite having apparent specific gravity of less than 1 and particle sizes of 0.3 mm to 1.4 mm and packed with a water-soluble film (Japanese Patent Laid-open No. Hei 9-183701). However, there may arise a problem in spreadability of the components because a portion of the formulation precipitates on the bottom at the point of the treatment, and a disadvantage that since much quantity of the agrochemically active ingredient still remain on the granular nucleus made of a foamed plastic material, pumice, calcined pearlite, or the like after the treatment, the desired effect of the agricultural chemicals can not be exhibited but, on the contrary, phytotoxicity may arise from bringing the agricultural chemicals gathered together by the wind.

Furthermore, a granular water-floatable insecticide in which an insecticide is coated on actatic polypropylene granules using a binder (Japanese Patent Publication No. Sho 45-9560), a floatable granular formulation in which an insecticide component is firmly fixed on calcined pearlite with polybutene (Japanese Patent Publication No. Sho 47-1240) are known, however, since much quantity of the agrochemically active ingredients remain on the granular nucleus, as similarly as above, the result is not only that the desired effect of the agricultural chemicals can not be exhibited but phytotoxicity may arise because the agricultural chemicals are gathered together by the wind.

In addition, in the conventional art, it has been difficult to obtain a scattering type formulation enabling labor-saving application containing agrochemically active ingredients which are liquid at room temperature.

SUMMARY OF THE INVENTION

In an agricultural chemicals formulation to be thrown directly into a rice paddy field filled with water to be scattered, an object of the present invention is to provide a composition having an excellent spreadability without stagnation of agrochemically active ingredients at the point of treatment, and in particular, to realize a labor-saving scattering (application) type formulation in a liquid state at room temperature containing agrochemically active ingredients, which has been hitherto difficult to realize, and further to make the formulation contain a high concentration of the agrochemically active ingredients in a liquid state at room temperature.

As a result of assiduous study to obtain a labor-saving scattering (application) type formulation containing an agrochemically active ingredient, especially that in a liquid state at room temperature, as an effective component, the present inventors have found that when the agrochemically active ingredient is made into a liquid matter together with a surfactant and a substance having a thickening function or a gelation function in the water, which is then packed with a water-soluble film after it is carried by a granular nucleus, it becomes possible to be scattered (applied) on a rice paddy field only by being thrown from a path between the paddy fields without entering into the paddy fields and, in addition, it has excellent spreadability, and based upon this finding, the inventors have accomplished the present invention.

The present invention is to provide an agricultural chemicals formulation for a rice paddy field, which is characterized by that a granular composition in which an active ingredient of the agricultural chemicals in a liquid state at room temperature, a surfactant, and a substance exhibiting a thickening function or a gelation function in the water are carried by granular nucleuses is packed with a water-soluble film.

In addition, the present invention is to provide a method of producing an agricultural chemicals formulation for a rice paddy field, comprising the steps of preparing a granular composition by letting a granular nucleus hold and carry a liquid agrochemically active ingredient at room temperature, a surfactant, and a substance exhibiting a thickening function or a gelation function in the water and packing thus obtained granular composition in a water-soluble film.

Furthermore, the present invention is to provide a method of scattering (applying) an agrochemically active ingredient, comprising the steps of throwing directly the agricultural chemicals formulation for a rice paddy field in a paddy field filled with water at a rate of 2 to 20 bags per 10 a.

DETAILED DESCRIPTION OF THE PREFERRED EMBODIMENTS

Figure 1:
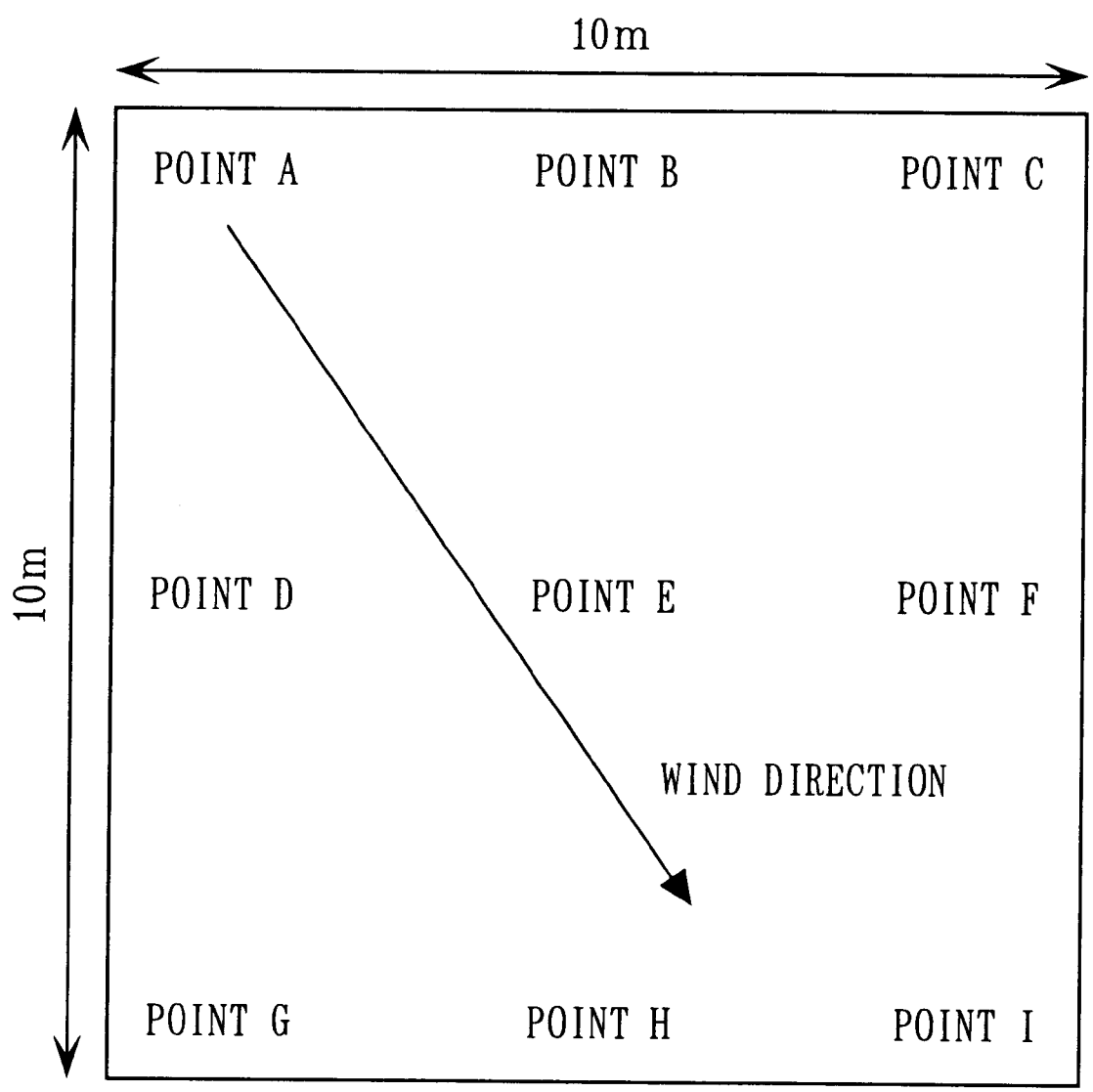
FIG. 1 shows a rice paddy field having an area of 10 m by 10 m, used in the test example 2. The point E in the drawing is a treatment point with an agricultural chemicals formulation for a rice paddy field.

In the present specification, an agrochemically active ingredient in a liquid state at room temperature includes an agrochemically active ingredient in a solid state at room temperature which is dissolved or dispersed in an adequate solvent as well as an originally liquid active ingredient of the agricultural chemicals at room temperature. A substance exhibiting a thickening function or a gelation function in the water refers to a substance exhibiting either one or both of these functions by the help of water.

The agricultural chemicals formulation for a rice paddy field of the present invention is such that a granular composition in which a liquid matter containing a liquid agrochemically active ingredient at room temperature, a surfactant, and a substance exhibiting a thickening function or a gelation function in the water (hereinafter such a liquid matter is referred to "a liquid agricultural chemicals formulation") is held and carried by a granular nucleus, is packed with a water-soluble film.

An agrochemically active ingredient used for the agricultural chemicals formulation for a rice paddy field is usable when it is in a liquid state as described above, and even when it is in a solid state it can be made usable as a liquid substance by dissolving or dispersing in a solvent. Therefore, the agrochemically active ingredient is not limited in particular, both solid chemicals and liquid chemicals, regardless of being readily soluble or slightly soluble in water, can be used so far as they can be generally used as agricultural chemicals. As such an agrochemically active ingredient, for instance, herbicide, fungicides, insecticide, PGR (plant growth regulator), and the like can be cited. Especially, substances advantageously used for a paddy treatment are preferable.

Among agrochemically active ingredients of the agricultural chemicals in the present invention, the examples which can be cited in a liquid state at room temperature are a herbicide such as 2-methyl-4-chlorophenoxy-thio acetic acid-s-ethyl(phenothiol), S-(4-chlorobenzyl)N,N-diethylthiocarbamate(benthiocarb), S-benzyl=1,2-dimethlpropyl(ethyl) thiocarbamate(esprocarb), S-ethylhexahydro-1H-azepin-1-carbothioate(molinate), 2-chloro-2',6'-diethyl-N-(butoxymethyl)acetanilide (butachlor), 2-chloro-2',6'-diethyl-N-(2-propoxyethyl) acetanilide(pretilachlor), ethyl 4-(4-chloro-o-tryloxy) butylate(MCPB-ethyl) and so on, a fungicide such as O,O-diisopropyl-S-benzylthiophosphate(IBP) and so on, insecticide such as O,O-dimethyl-O-(3-methyl-4-nitrophenyl)thiophosphate(MEP), (2-isopropyl-4-methylpyrimidyl-6)-diethylthiophosphate(diazinon), dimethyldicarbethoxyethyldithiophosphate(malathion), O,O-dipropyl-O-4-methylthiophenylphosphate(propaphos), 2,3-dihydro-2,2-dimethyl-7-benzo[b]flanyl=N-dibutylaminothio-N-methylcarbamate(carbosulfan), ethyl=n-[2,3-dihydro-2,2-dimethylbenzoflan-7-yloxycarbonyl (methyl)aminothio]-N-isopropyl-.beta.-alanynate (benfuracarb), (RS)-.alpha.-cyano-3-phenoxybenzyl=(RS)-2,2-dichloro-1-(4-ethoxyphenyl)cyclopropane carboxylate (cycloprothrin) can be cited for each kind of chemicals.

As an example of a solid agrochemical active ingredient at room temperature among the agricultural chemicals ingredients used in the present invention, a herbicide such as 2,4,6,-trichlorphenyl-4'-nitrophenylether(CNP), .alpha.-(2-naphthoxy)propionanilide (naproanilide), 5-(2,4-dichlorophenoxy)-2-nitrobenzoate methyl(bifenox), S-1-methyl-1-phenylethyl=piperidine-1-carbothioate (dimepypelate), O-3-tert-butylphenyl=6-methoxy-2-pyridyl (methyl)thiocarbamate(pyributicarb), (RS)-2-bromo-N-(.alpha.,.alpha.-dimethylbenzyl)-3,3-dimethylbutylamide (bromobuthyde), 2-benzothiazol-2-yloxy-N-methylacetanilide(mefenacet), 1-(.alpha.,.alpha.-dimethylbenzyl)-3-(paratryl)urea(dimron), methyl=.alpha.-(4,6-dimethoxypyrimidine-2-ylcarbamoylsulfamoyl)-O-toluate (bensulfuron-methyl), 1-(2-cloroimidazo[1,2-a] pyridine-3-ylsulfonyl)-3-(4,6-dimethoxypyrimidine-2-yl) urea(imazosulflon), ethyl=5-(4,6-dimethoxypyrimidine-2-ylcarbamoylsulfamoyl)-1-methylpyraso 1-4-carboxylate (pyrazosulfaron-ethyl), 2methythio-4,6-bis(ethylamino)-s=triazine(simetiyne), 2-methylthio-4,6-bis (isopropylamino)-s-triazine(prometryn), 2-methylthio-4-ethylamino-6-(1,2-dimethylpropylamino)-s-triazine(dimethametryn), 2,4-dichlorophenyl-3'-methoxy-4'-nitrophenylether (chlomethoxynil), 5-tert-butyl-3-(2,4-dichoro-5-isopropoxyphenl)-1,3,4-oxadiazorin-2-one(oxadiazon), 4-(2,4-dichlorobenzoyl)-1,3-dimethyl-5-pyrazoryl-p-toluensulfonate(pyrazolate), 2-[4-(2,4=dichlorobenzoyl)-1, 3-dimethylpyrazole-5-yloxy]acetophenone(pyrazoxyfen), (RS)-2-(2,4-dichloro-m-tolyloxy)propionanilide clomeprop), 2-[4-[2,4-dichloro-m-toluoyl)-1,3-dimethylpyrazole-5-yloxy]-4'-methylaceto phenon (benzofenap), S,S'-dimethyl=2-difluoromethyl-4-isobutyl-6-trifluoromethylpyridine-3,5-dicarbothioate (dithiopyl), 2-chloro-N-(3-methoxy-2-thenyl)-2',6'-dimethylacetanilide (thenylchlor), n-butyl-(R)-2-[4-(2-fluoro-4-cyanophenoxy) phenoxy]propionate(cyhalofop-butyl), 3-[1 -(3,5-dichlorphenyl)-1-methylethyl]-2,3-dihydro-6-methyl-5-phenyl-4H-1,3-oxazine4-one(oxaziclomefone), 3-(4-chloro-5-cyclopentyloxy-2flyorophenyl)-5-isopropyridene-1,3-oxazolidine-2,4-dione (pentoxazone), 1-(diethylcarbamoyl)-3-(2,4,6-trimethylphenylsulfonyl)-1,2,4-triazole (cafenstrole), N-{[(4,6-dimethoxypyrimidine-2-yl) aminocarbonyl]}-1-methyl-4-(2-methyl-2H-tetrazole-5-yl) (cafenstrole), methyl 2-[(4,6-dimethoxypyrimidine-2-yl) oxy]-6-[(E)-1-(methoxyimino)ethyl] benzoate (pyriminobac-methyl), 4-(2-chloro-phenyl)-5-oxo-4, 5dihydro-tetrazole-1-carboxylic acid cyclohexyl-ethyl-amide (fentrazamide) and so on, a fungicide such as 3'-isopropoxy-2-methylbenzanilide (mepronil), .alpha., .alpha.,.alpha.-trifluoro-3'-isopropoxy-O-toluanilide (flutolanil), 3,4,5,6-tetrachloro-N-(2,3-dichlorophenyl) phthalamid acid(tecloftalam), 1-(4-chlorobenzyl)-1-cyclopentyl-3-pheny urea 25 (pencycuron), 6-(3,5-dichloro-4-methylphenyl)-3 (2H)-pyridazinone(diclomezin), methyl=N-(2-methoxyacetyl)-N-(2,6-xylyl)-DL-alaninate (metalaxyl), (E)-4-chloro-.alpha.,.alpha.,.alpha.-trifluoro-N-(1-imidazole-1-yl-2-propoxyet hylidene)-o-toluidine (triflumizole), [5-amino-2-methyl-6-(2,3,4,5,6-pentahydroxycyclohexycyloxy)tetrahydropylan-3-yl]

amino-.alpha.-iminoacetic acid(kasugamycin), baridamicine, 3-aryloxy-1,2-benzoisothiazole-1,1-dioxyd (probenazole), diisopropyl-1,3-dithiolan-2-ylidene-malonate(isoprothiolane), 5-methyl-1,2,4-triazoro [3,4-b] benzothiazole(tricyclazole), 1,2,5,6-tetrahydropylolo[3,2,1-ij]chinoline-4-one (pyroquilon), 5-ethyl-5,8-dihydro-8-oxo[1,3]dioxolo[4,5-g]chinoline-7-carboxylic acid 5(oxolinic acid), (Z)-2'-methylacetophenone=4,6-dimethylpyrimidin-2-ylhydrazone 4,5,6,7-tetrachlorophthalide(ferimzone), 3-(3,5-dichlorophenyl)-N-isopropyl-2,4-dioxoimidazolidine-1-carboxyamide(iprodione), and so on, insecticide such as 1-naphthyl-N-methylcarbamate(NAC), O,O-diethyl-O-(3-oxo-2-phenyl-2H-pyridadine-6-yl) phosphorothioate(pyridaphenthion), O,O-dimethyl-O-3,5,6-trichoro-2-pyridylphosphorothioate(chlorpyrifos-methyl), O,O-dimethyl-S-(N-methylcarbamoylmethyl) dithiophosphate(dimethoate), O,S-dimethyl-N-acetylphosphoroamidethioate(acephate), ethylparanitrophenylthiono bennzene phosphonate (EPN), 2-secondary-butylphenyl-N-methyylcarbamate(BPMC), 2-(4-ethoxyphenyl)-2-methylpropyl=3-phenoxybenzyl=ether (etofenprox), 1,3-bis (carbamoylthio)-2-(N,N-dimthylamino)propane hydrochloride(cartap), 5-dimethylamino-1,2,3-trithian oxalate(thiocyclam), S,S'-2-dimetylamino trimethylene=di(benzenthiosulfonate) (bensultap), 2-tert-butylimino-3-isopropyl-5-phenyl-1,3,5,6 tetrahydro-2H-1,3,5-thiadiazine-4-one(buprofezin), and so on, and a plant growth adjuster such as 4'-chloro-2'-(.alpha.-hydroxybenzyl)isonicotinanilide(inabenfide), (2RS, 3RS)-1-(4-chlorophenyl)-4,4-dimethyl-2-(1H-1,2,4-triazole-1-yl) pentane-3-ol (paclobutrazol), (E)-(S)-1-(4-chlorophenyl)4,4-dimethyl-2-(1H-1,2,4-triazole-1-yl)penta-1-ene-3-ol (uniconazole) can be cited. However, the agrochemically active ingredients in the present invention are not limited to these chemicals described above.

Further, such an agrochemically active ingredient of the agricultural chemicals can be used alone or as a mixture of two kinds or more. As the total amount of the agrochemically active ingredients blended in the agricultural chemicals, 0.1 parts by weight to 70 parts by weight for 100 parts by weight of the granular composition is generally preferable.

In the present invention, when the agrochemically active ingredient of the agricultural chemicals is liquid at room temperature, it can be used as it is, but when it is a solid at room temperature, it is necessary to use after converting it into a liquid state by dissolving it or dispersing it into a solvent. As a solvent capable of being used to dissolve or disperse a solid agrochemically active ingredient of the agricultural chemicals, any solvent generally used for an agricultural chemicals formulation can be used as far as it does not react with a dissolved substance, and does not dissolve a water-soluble film. As a concrete example of the solvent, an organic solvent such as dioctylphthalate, methylnaphthalene, alkyl pyrolidone, phenylxyrylethane, glycerine, alkylene glycol, xylene, kerosine, machine oil, methane series hydrocarbon, fatty acid ester, polybasic acid, coconut oil, soybean oil, rapeseed oil, and silicone oil, and furthermore, above-described agrochemically active ingredients in a liquid state at room temperature can be cited. Especially, the solvent having a specific gravity of 1 or less is preferable. As the compounding amount of these solvents, a range from 10 parts by weight to 200 parts by weight for 100 parts of the solid active ingredients of the agricultural chemicals is preferable in general. These solvents can be used for an additive to an agrochemically active ingredient of the agricultural chemicals in a liquid state at room temperature, as necessary.

The agricultural chemicals formulation for a rice paddy field of the present invention is required to contain a substance exhibiting a thickening function or a gelation function in the water (hereinafter, referred to "thickening/gelation substance"). In the present invention, as will be described later, the thickening/gelation substance has a function to bond the granular nucleuses together by temporarily performing as a bonding agent by the help of water after the formulation of the present invention is ton into water, but has no function to fix the agrochemically active ingredients of the agricultural chemicals firmly to the granular nucleuses. Accordingly, the thickening/gelation substance exists alone on the surface of the granular nucleus, unrelated to the active ingredients of the agricultural chemicals.

In the present invention, a water-soluble polymer can be used as a substance which has a thickening function mainly in water, among the thickening/gelation substances. As a usable water-soluble polymer, it is preferable to be a solid at room temperature, more preferably a powdery substance, and any substance can be used, provided that it is not soluble in the above-described active components of the agricultural chemicals which are liquid at room temperature. Especially, the substance having the viscosity in 1% aqueous solution of 100 mPa·s or more is preferable, and more preferably, 1000 mPa·s or more.

As concrete examples of the water-soluble polymer, sodium polyacrylate having a molecular weight of 5000 or more, .alpha.-modified starch, dextrin, polyvinyl alcohol, carboxymethyl cellulose, xanthan gum, gum arabic, polyvinyl pyrolidone, and polyalkylene glycol having a molecular weight of 100,000 or more can be cited but it is not limited to these substances. These water-soluble polymer can be used alone or as a mixture of two kinds or more.

A substance having mainly a gelation function among the thickening/gelation substances used in the present invention is preferably used as a mixture with a component slightly soluble in water among the agrochemically active ingredients of the agricultural chemicals in a liquid state at room temperature. Especially, it is preferable to use a gelation substance having water repellancy. Any water repellent substance can be used, provided that is a powdery substance in a solid state at room temperature and is not soluble in the above-described active ingredients of the agricultural chemicals in a liquid state at room temperature.

As concrete examples of the water-repellant substances, salt of fatty acid such as magnesium stearate, calcium stearate, sodium oleate, and hydrophobic silica and so on can be cited. A water-repellant substance in a liquid state including higher alcohol such as stearyl alcohol, higher fatty acid such as stearic acid, silicon oil and its derivatives, fluorine series surfactants, liquid paraffin can be used as a powder by being adsorbed to fine powders having adsorptivity such as white carbon, activated carbon, diatmite and so on.

In general, the blending amount of the thickening/gelation substance exhibiting a thickening function or a gelation function in the water is preferably 0.1 parts by weight to 20 parts by weight for 100 parts by weight of the granular composition, and more preferably, 0.5 parts by weight to 10 parts by weight for 100 parts by weight of the granular composition.

In order to obtain a desirable dispersion of the agrochemically active ingredients of the agricultural chemicals in water after the formulation being thrown into a paddy field, a surfactant is contained in the agricultural chemicals formulation for a rice paddy field of the present invention. As a usable surfactant, a substance generally used in the agricultural chemicals can be cited. As concrete examples of the surfactants, nonionic surfactant such as polyethylene glycol higher fatty acid ester, polyoxyethylene alkylether, polyoxyethylene alkylarylether, polyoxyethylenearylphenylether, sorbitanmonoalkylate, acetylene alcohol, acetylene diol, and alkylene oxide additives thereof; anionic surfactant such as alkylaryl sulfonate, dialkyl sulfonate, lignin sulfonate, naphthalene sulfonate and its condensate, alkyl sulfate ester, alkyl phosphate ester, alkylarylsulfate ester, alkylaryl phosphate ester, polyoxyethylene alkylether sulfate ester, polyoxyethylene alkylarylether sulfate ester, polyoxyethylene arylphenylether sulfate ester, polycarboxylic acid type polymer surfactant, further a silicone series surfactant, fluorine series surfactant can be cited. These surfactants can be used alone or as a mixture of two kinds or more.

The rate of these surfactants to be used in the formulation is generally from 0.1 parts by weight to 30 parts by weight for 100 parts by weight of the granular composition, preferably from 0.5 parts by weight to 20 parts by weight, more preferably from 2 parts by weight to 10 parts by weight.

The above agrochemically active ingredient of the agricultural chemicals, the surfactant, and the thickening/gelation substance can be made a liquid agricultural chemicals formulation by mixing these materials according to the ordinary method. For instance, a liquid agrochemically active ingredient of the agricultural chemicals at room temperature, a thickening/gelation substance, a surfactant, a solid agrochemically active ingredient of the agricultural chemicals at room temperature as necessary are mixed together, and further other adjuvant to be described later are added to them, as necessary, thereby obtaining a liquid agricultural chemicals formulation as a liquid mixture or a suspended liquid matter.

Its granular composition can be obtained by allowing the liquid agricultural chemicals formulation to be held and carried by a granular nucleus. In such a case, the indispensable components of the liquid agricultural chemicals formulation are not always required to be carried by the granular nucleus simultaneously, but they may be carried one by one. For instance, the granular nucleus are first added to the agrochemically active ingredients of the agricultural chemicals in a liquid state at room temperature and mixed together, and then a mixture of the surfactants and others is added to the above mixture. Thus, the granular composition may be obtained by allowing each component to be carried by the granular nucleus one by one.

The granular nucleus used to obtain the above-described granular composition are solid base material which can hold and carry the above liquid agricultural chemicals formulation. As a granular nucleus to be used for holding and carrying the liquid agricultural chemicals in the present invention, water-insoluble solid carriers can be cited. For instance, mineral matter such as pumiceous sand, vermiculite, pearlite can be used. However, it is especially preferable to use a piece of vegetable matter such as rice hull, sugar cane, rice straw, wheat straw, coconut, banana, bamboo, reed, kenaf, corn nucleus, and wood, because they have undergone time-varying corrosive decomposition.

The granular nucleus having the shorter diameter of 0.1 mm to 10 mm and bulk specific gravity of 1 or less are preferable. The ratio of the shorter diameter to the longer diameter is between 1 to 20 in general. Usually 5 parts by weight to 60 parts by weight of these granular nucleuses are contained in 100 parts by weight of the composition, and the content of 10 parts by weight to 50 parts by weight is more desirable.

In the present invention, in addition to the above-described indispensable components, substances usually used in an agricultural chemicals formulation such as a filler, active ingredient stabilizer, physical property improvement agent can be used as supplementary additives as necessary, and these additives can be added as needed during the production process of the granular composition. These additives can be in a solid state or in a liquid state, and can be slightly soluble or readily soluble in water.

As these supplementary additives, fine mineral particles such as clay, calcium carbonate, bentonite, talc, diatomite, and white carbon; organic or inorganic salt such as ammonium sulfate, ammonium bicarbonate, ammonium nitrate, ammonium chloride, potassium chloride, sodium sulfate, magnesium sulfate, sodium citrate, sodium carbonate, sodium hydrogen carbonate, organic acids such as citric acid, and succinic acid, sugars such as cane sugar, lactose, xanthan gum, water-soluble fine powders such as urea, expanded shirasu made of shirasu, inorganic substances such as filite made of calcined alminosilicates, microbaloons which are made by expanding sodium silicate or borax, fly ash, pumice, ceramic hollow body, and so on, phenol microbaloon made by phenol resin, echo-sphere made of epoxy resin, polyurethane foam made from polyurethane, microsphere made of vinylidene chloride and acrylonitrile copolymer and so on can be cited. Thus, a hollow body or dyestuff having 10 μm to 600 μm in particle diameter, and having single, or two or more independent foams can be cited, but it is not limited to these substances.

As described above, the agricultural chemicals formulation for a rice paddy field of the present invention can be prepared by packing a granular composition with a water-soluble film. The granular composition is made of a liquid agrochemically active ingredient of the agricultural chemicals, a surfactant, a thickening/gelation substance and so on carried by a granular nucleus. The packing with a water-soluble film is carried out in a manner that, for instance, the granular composition is packed in a water-soluble film bag, which is closed by heat-sealing or with adhesives.

More concretely, for instance, a water-soluble film sheet is bent to make a bag with a heat sealer, to which the granular composition is filled in. Then the opening of the bag is sealed with a heat sealer and the like so. that the agricultural chemicals formulation of the present invention can be obtained.

A suitable water-soluble film to be used in the present invention is a film which is dissolved or dispersed rapidly into water. As a film material, polyvinyl alcohol, polyoxy polyalkylene glycol, hydroxypropylcellulose, hydroxypropylmethylcellulose, methylcellulose, sodium carboxymethylcellulose, sodium polyacrylate, alginic acid, gelatine, pulran, soluble starch are cited as examples. However, it is not limited to these materials, so far as they are not dissolved in the above-described active ingredients of the agricultural chemicals in a liquid state at room temperature and the surfactant in the liquid agricultural chemicals formulation.

The thickness of the water-soluble film used for the packing of the composition is not particularly limited, however it is generally preferable to have the thickness of 20 μm to 100 μm. It is also acceptable to pack in multiple layers with water-soluble films of the same composition or different composition. In order to restrain formation of an air dome, and to make the dissolution of the water-soluble film better when the treatment is carried out, it is acceptable to make holes of 0.1 mm to 1 mm in diameter in the water-soluble film at a rate of 1 to 100 per bag of the agricultural chemicals formulation. Alternatively, a gap to make air pass through may be provided on the heat sealing portion when the heat sealing is carried out as will be described later.

The agricultural chemicals for a rice paddy field of the present invention thus obtained preferably have a weight of 10 g to 200 g per a bag, and are used by directly throwing 2 to 20 bags per 10 a., preferably 5 to 20 bags, into a paddy field filled with water from a path between rice fields or a water inlet.

The present invention is characterized by that the liquid matter blended with the thickening/gelation substance exhibiting a thickening function or a gelation function in the water is held and carried by the granular nucleus having a specific size, enabling it to be a floating formulation on the surface of water without using a large quantity of organic solvent or excess amount of the granular nucleus, so that preparation of the formulation can be realized, which enables it to be scattered in a small quantity.

When the agricultural chemicals formulation of the present invention is thrown into a paddy field, water comes into the water-soluble film. Then, the granular nucleus are temporarily bonded together by the help of the thickening/gelation substance as a bonding agent, which is attached on the surface of the granular nucleus. At this time, a granular nucleus having a large buoyancy is attached with a granular nucleus having a small buoyancy and floats on the surface of the water. Then, the whole water-soluble film is dissolved into water and the granular nucleus being put together is dispersed while being spread on the surface of the water by the help of the surfactant. Since the agrochemically active ingredients of the agricultural chemicals are dispersed into water after detaching from the granular nucleus, it becomes possible to spread and scatter (apply) the agrochemically active ingredient of the agricultural chemicals formulation in the whole paddy field. It should be noted that in a case when the formulation is scattered in a granular composition without using a water-soluble film, the effect of the present invention can not be expected, because the thickening/gelation substance does not serve as a bonding agent.

Hereinafter, the present invention will be explained in detail with examples and test examples. However, the present invention is not limited to the examples. Incidentally, the word "part" indicates "part by weight" in the following examples.

EXAMPLE 1

A liquid agricultural chemicals formulation obtained by mixing 51 parts of IBP, 2.5 parts of polyoxyethylene non-ylphenyl ether and 4 parts of lignin sulfonate and 5 parts of denatured dextrin powder (amicole No. 1B; Nichiden Chemicals Co. Ltd.) is mixed with 37.5 parts of wood piece (shorter diameter 1 mm to 3 mm, longer diameter 4 mm to 8 mm, bulk specific gravity 0.12) to obtain granular matter which is packed in a water-soluble film made of polyvinyl alcohol at a rate of 100 g of the granular matter per one bag. The above-described bag is heat-sealed to obtain the agricultural chemicals formulation for a rice paddy field of the present invention. The agricultural chemicals formulation for a rice paddy field of this example is scattered at a rate of 10 bags per 10 a.

EXAMPLE 2

A liquid agricultural chemicals formulation obtained by mixing 30 parts of benthiocarb, 4.8 parts of MCPB-ethyl, 9 parts of simetryne, 9 parts of mefenacet, 1 part of polyoxyethylene styrylphenyl ether sulfate, 1 part of polyoxyethylene alkylphenylether sulfate, 0.2 parts of dioctylsulfosuccinate, 2 parts of acetylene alcohol, and 3 parts of powdery xanthan gum is mixed with 40 parts of rice hulls (shorter diameter 1 mm to 3 mm, longer diameter 4 mm to 6 mm, bulk specific gravity 0.11) to obtain granular matter which is packed in a water-soluble film made of polyvinyl alcohol at a rate of 25 g of the granular matter per one bag. The above-described bag is heat-sealed to obtain the agricultural chemicals formulation for a rice paddy field of the present invention. The agricultural chemicals formulation for a rice paddy field of this example is scattered at a rate of 20 bags per 10 a.

EXAMPLE 3

A liquid agricultural chemicals formulation obtained by mixing 42.9 parts of benthiocarb, 1.5 parts of bensulfuron-methyl, 8.6 parts of mefenacet, 1.2 parts of ammonium polyoxyethylene arylphenylethersulfate, 1.5 parts of ammonium polyoxyalkylether sulfate, 2.3 parts of dialkylsulfosuccinate, 1 part of sodium polyacrylate powder having a molecular weight of 1,000,000, is mixed with 41 parts of kenaf piece (shorter diameter 0.5 mm to 2 mm, longer diameter 2 mm to 10 mm, bulk specific gravity 0.06) to obtain granular matter which is packed in a water-soluble film made of polyvinyl alcohol at a rate of 35 g of the granular matter per one bag. The above-described bag is heat-sealed to obtain the agricultural chemicals formulation for a rice paddy field of the present invention. The agricultural chemicals formulation for a rice paddy field of this example is scattered at a rate of 10 bags per 10 a.

EXAMPLE 4

A liquid agricultural chemicals formulation obtained by mixing 42.9 parts of benthiocarb, 1.5 parts of bensulfuron-methyl, 8.6 parts of mefenacet, 1.2 parts of ammonium polyoxyethylene arylphenylethersulfate, 1.5 parts of ammonium polyoxyalkylether sulfate, 2.3 parts of dialkylsulfosuccinate, 3 parts of calcium stearate powder, is mixed with 41 parts of kenaf piece (shorter diameter 0.5 mm to 2 mm, longer diameter 2 mm to 10 mm, bulk specific gravity 0.06) to obtain granular matter which is packed in a water-soluble film made of polyvinyl alcohol at a rate of 35 g of the granular matter per one bag. The above-described bag is heat-sealed to obtain the agricultural chemicals formulation for a rice paddy field of the present invention. The agricultural chemicals formulation for a rice paddy field of this example is scattered at a rate of 10 bags per 10 a.

EXAMPLE 5

A liquid agricultural chemicals formulation obtained by mixing 42.9 parts of benthiocarb, 1.5 parts of bensulfuron-methyl, 8.6 parts of mefenacet, 1.2 parts of ammonium polyoxyethylene arylphenylethersulfate, 1.5 parts of ammonium polyoxyalkyether sulfate, 2.3 parts of dialkylsulfosuccinate, 12 parts of ceramic hollow body (grain size 100 μm to 125 μm), 1 part of .alpha.-modified starch powder (amicole K; Nichiden Chemicals Co. Ltd.), is mixed with 30 parts of kenaf piece (shorter diameter 0.5 mm to 2 mm, longer diameter 2 mm to 10 mm, bulk specific gravity 0.06) to obtain granular matter which is packed in a water-soluble film made of polyvinyl alcohol at a rate of 35 g of the granular matter per one bag. The above-described bag is heat-sealed to obtain the agricultural chemicals formulation for a rice paddy field of the present invention. The agricultural chemicals formulation for a rice paddy field of this example is scattered at a rate of 10 bags per 10 a.

EXAMPLE 6

A liquid agricultural chemicals formulation obtained by dissolving 5 parts of cyhalofop-butyl into 21 parts of adipic acid diisodecylester, and then by mixing 7 parts of caffenstrol, 13.3 parts of dimron, 1.7 parts of bensulfuron-methyl, 1 part of polyoxyethylene styrylphenylether sulfate, 3 parts of lignin sulfonate, 2 parts of acetylene alcohol, 5 parts of methane series hydrocarbon, and 1 part of sodium polyacrylate powder having a molecular weight of 1,000,000 to the above solution, is mixed with 40 parts of kenaf piece (shorter diameter 0.5 mm to 2 mm, longer diameter 2 mm to 10 mm, bulk specific gravity 0.06) to obtain granular matter which is packed in a water-soluble film made of polyvinyl alcohol at a rate of 60 g of the granular matter per one bag. The above-described bag is heat-sealed to obtain the agricultural chemicals formulation for a rice paddy field of the present invention. The agricultural chemicals formulation for a rice paddy field of this example is scattered at a rate of 5 bags per 10 a.

EXAMPLE 7

A liquid agricultural chemicals formulation obtained by mixing 24 parts of tricyclazol, 24 parts of methane series hydrocarbon, 2 parts of polyoxyalkylene arylphenylether sulfonate, 3 parts of condensation product of butylnaphthalene sulfonic acid and formalin, and 2 parts of polyalkylene glycol powder having a molecular weight of 100,000, is mixed with 45 parts of pearlite (shorter diameter 0.3 mm to 1.2 mm, longer diameter 0.3 mm to 1.2 mm, bulk specific gravity 0.2) to obtain granular matter which is packed in a water-soluble film made of polyvinyl alcohol at a rate of 50 g of the granular matter per one bag. The above-described bag is heat-sealed to obtain the agricultural chemicals formulation for a rice paddy field of the present invention. The agricultural chemicals formulation for a rice paddy field of this example is scattered at a rate of 10 bags per 10 a.

EXAMPLE 8

A liquid agricultural chemicals formulation obtained by mixing 1.5 parts of bensulfuron-methyl, 24 parts of mefenacet, 2.4 parts of dioctylsulfosuccinate, 0.1 parts of polyoxyethylene styrylphenylphether, 3 parts of butylene and maleic acid copolymer salt, 25.5 parts of adipic acid isodecyl, 1 part of sodium polyacrylic acid powder having a molecular weight of 1,000,000, is mixed with 41.5 parts of kenaf piece (shorter diameter 0.5 mm to 2 mm, longer diameter 2 mm to 10 mm, bulk specific gravity 0.06) to obtain granular matter which is packed in a water-soluble film made of polyvinyl alcohol at a rate of 50 g of the granular matter per one bag. The above-described bag is heat-sealed to obtain the agricultural chemicals formulation for a rice paddy field of the present invention. The agricultural chemicals formulation for a rice paddy field of this example is scattered at a rate of 10 bags per 10 a.

A liquid agricultural chemicals formulation obtained by dissolving 7.5 parts of etofenprox into 30 parts of phenylxyrylethane, and then mixing 2 parts of polyoxyalkylene arylphenylether sulfonate, 3 parts of condensation product of butylnaphthalene sulfonic acid and formalin, 1 part of sodium polyacrylic acid powder having a molecular weight of 1,000,000, 1 part of calcium stearate powder, is mixed with 55.5 parts of kenaf piece (shorter diameter 0.5 mm to 2 mm, longer diameter 2 mm to 10 mm, bulk specific gravity 0.06) to obtain granular matter which is packed in a water-soluble film made of polyvinyl alcohol at a rate of 30 g of the granular matter per one bag. The above-described bags are heat-sealed. Then, each bag is provided with 10 holes having a diameter of 0.5 mm on a water-soluble film to obtain the agricultural chemicals formulation for a rice paddy field of the present invention. The agricultural chemicals formulation for a rice paddy field of this example is scattered at a rate of 10 bags per 10 a.

A liquid agricultural chemicals formulation obtained by mixing 42.9 parts of benthiocarb, 1.5 parts of bensulfuron-methyl, 8.6 parts of mefenacet, 1.2 parts of ammonium polyoxyethylene arylphenylethersulfate, 1.5 parts of ammonium polyoxyalkyether sulfate, and 2.3 parts of dialkylsulfosuccinate, is mixed with 42 parts of kenaf piece (shorter diameter 0.5 mm to 2 mm, longer diameter 2 mm to 10 mm, bulk specific gravity 0.06) to obtain granular matter which is packed in a water-soluble film made of polyvinyl alcohol at a rate of 35 g of the granular matter per one bag. The above-described bag is heat-sealed to obtain the agricultural chemicals formulation.

A liquid agricultural chemicals formulation obtained by mixing 42.9 parts of benthiocarb, 1.5 parts of bensulfuron-methyl, 8.6 parts of mefenacet, 1.2 parts of ammonium polyoxyethylene arylphenylethersulfate, 1.5 parts of ammonium polyoxyalkyether sulfate, and 2.3 parts of dialkylsulfosuccinate, 1 part of sodium polyacrylate powder having a molecular weight of 1,000,000 is mixed with 41 parts of kenaf piece (shorter diameter 0.5 mm to 2 mm, longer diameter 2 mm to 10 mm, bulk specific gravity 0.06) to obtain a granular agricultural chemicals formulation.

A liquid agricultural chemicals formulation obtained by mixing 1.5 parts of bensulfuron-methyl, 24 parts of mefenacet, 2.4 parts of dioctylsulfosuccinate, 0.1 parts of polyoxyethylene styrylphenylphether, 3 parts of butylene and maleic acid copolymer salt, 25.5 parts of adipic acid isodecyl ester is mixed with 43.5 parts of kenaf piece (shorter diameter 0.5 20 mm to 2 mm, longer diameter 2 mm to 10 mm, bulk specific gravity 0.06) to obtain granular matter which is packed in a water-soluble film made of polyvinyl alcohol at a rate of 50 g of the granular matter per one bag. The above-described bag is heat-sealed to obtain the agricultural chemicals formulation.

TEST EXAMPLE 1

Occurring of Precipitation of the Agricultural Chemicals Formulation on the Point of the Scattering thereof.

The agricultural chemicals formulations for a rice paddy field of the present invention described in Examples 1 to 9, and the agricultural chemicals formulation described in Comparisons 1 to 3, are scattered (applied) in the center of a paddy field having 5 cm in depth and 2 m×2 m in area. One hour after the scattering (application), existence of the granular nucleus precipitated on the bottom of the scattered (applied) point is observed by the unaided eye with reference to the standard described below. The result is shown in Table 1.

TABLE 1

| AGRICULTURAL CHEMICALS FORMULATIONS FOR A RICE PADDY FIELD | EXISTENCE OF PRECIPITATION ON THE BOTTOM OF THE SCATTERED POINT |
|---|---|
| EXAMPLE 1 | ± |
| EXAMPLE 2 | ± |
| EXAMPLE 3 | − |
| EXAMPLE 4 | − |
| EXAMPLE 5 | ± |
| EXAMPLE 6 | − |
| EXAMPLE 7 | − |
| EXAMPLE 8 | − |
| EXAMPLE 9 | ± |
| COMPARISON 1 | ++ |
| COMPARISON 2 | ++ |
| COMPARISON 3 | ++ |

(Standard of Evaluation)
Mark for evaluation: Description
−: No precipitate is observed
±: A slight precipitate is observed
+: About 10% of the chemicals thrown are precipitated
++: About 50% of the chemicals thrown are precipitated As shown in Table 1, the amount of the precipitate on the bottom of water is small in the formulations of Examples 1 to 9, but is large in the formulations of Comparisons 1 to 3.

TEST EXAMPLE 2

Uniformity of the Constituents, Concentration of the Soil Surface Layer

The agricultural chemicals formulations for a rice paddy field of the present invention described in Examples 3, 4, 8 and the agricultural chemicals formulation described in Comparisons 1 to 3, are thrown and scattered in E point of the paddy field having 5 cm in depth and 10 m×10 m in area shown in FIG. 1. After 24 hours, water samples are withdrawn from points (A to I) shown in FIG. 1 and analyzed. The ratio of concentration of the agrochemically active ingredient obtained by analyzing the sample to the theoretical concentration when the agrochemically active ingredient is uniformly dispersed in the water is determined on the assumption that the above theoretical concentration would be 100%. Further, the degree of variability is calculated by dividing the standard deviation of the concentration in water in each point by the mean value.

The soil in each point in the extent of 10 cm in diameter and 5 cm in depth is withdrawn with a portion of water after 24 hours of the scattering (application) and is analyzed to obtain the ratio of concentration of the active ingredient of the agricultural chemicals obtained thus to the theoretical concentration when the agrochemically active ingredient is uniformly dispersed in the soil is determined on the assumption that the above theoretical concentration would be 100%. During the test, the water temperature is from 18° C. to 24° C., and the wind is blowing at the velocity of 2 to 6 m from the point A to the point 1. The result is shown in Table 2 and Table 3.

TABLE 2

| | BENTIOCARB (UNDER WATER/ SOIL SURFACE LAYER) | BENSULFURON-METHYL (UNDER WATER/SOIL SURFACE LAYER) | MEFENACET (UNDER WATER/ SOIL SURFACE LAYER) |
|---|---|---|---|
| EXAMPLE 3 | | | |
| POINT A | 60/34 | 76/11 | 49/44 |
| POINT B | 55/30 | 80/5 | 40/52 |
| POINT C | 60/25 | 71/6 | 38/46 |
| POINT D | 58/21 | 72/6 | 32/36 |
| POINT E | 55/34 | 69/14 | 41/52 |
| POINT F | 64/37 | 74/4 | 40/43 |
| POINT G | 60/31 | 65/7 | 36/54 |
| POINT H | 59/24 | 70/10 | 45/46 |
| POINT I | 64/27 | 66/8 | 39/40 |
| MEAN VALUE (%) | 59.4/29.2 | 71.4/7.9 | 40.0/45.9 |
| DEGREE OF VARIABILITY (%) | 5.5/18.3 | 6.6/40.8 | 12.2/13.0 |
| EXAMPLE 4 | | | |
| POINT A | 54/27 | 69/6 | 50/36 |
| POINT B | 62/29 | 66/10 | 42/44 |
| POINT C | 63/40 | 74/12 | 41/39 |
| POINT D | 59/31 | 69/6 | 45/48 |
| POINT E | 58/42 | 80/16 | 38/55 |
| POINT F | 65/24 | 73/8 | 38/40 |
| POINT G | 60/33 | 75/7 | 42/38 |
| POINT H | 60/31 | 71/11 | 49/36 |
| POINT I | 55/22 | 79/13 | 36/49 |
| MEAN VALUE (%) | 59.6/31.0 | 72.9/9.9 | 42.3/42.8 |
| DEGREE OF VARIABILITY (%) | 6.0/21.5 | 6.4/34.8 | 11.5/15.5 |
| EXAMPLE 8 | | | |
| POINT A | — | 74/5 | 48/44 |
| POINT B | — | 84/6 | 35/30 |
| POINT C | — | 76/8 | 38/40 |
| POINT D | — | 77/11 | 40/44 |
| POINT E | — | 81/10 | 45/36 |
| POINT F | — | 80/15 | 39/54 |
| POINT G | — | 63/11 | 36/36 |
| POINT H | — | 69/10 | 42/32 |
| POINT I | — | 71/10 | 47/42 |
| MEAN VALUE (%) | — | 75.0/9.6 | 41.1/39.8 |
| DEGREE OF VARIABILITY (%) | — | 8.7/31.0 | 11.4/1 8.4 |

NOTE) THE EXPRESSIONS INCLUDING A SLASH MARK IN THE TABLE INDICATE (CONCENTRATION % IN THE WATER/CONCENTRATION % IN THE SURFACE LAYER OF THEE SOIL)

TABLE 3

| | BENTIOCARB (UNDER WATER/ SOIL SURFACE LAYER) | BENSULFURON-METHYL (UNDER WATER/SOIL SURFACE LAYER) | MEFENACET (UNDER WATER/ SOIL SURFACE LAYER) |
|---|---|---|---|
| COMPARISON 1 | | | |
| POINT A | 32/12 | 70/5 | 32/26 |
| POINT B | 31/21 | 63/5 | 36/34 |
| POINT C | 40/11 | 70/10 | 55/31 |
| POINT D | 24/11 | 62/8 | 39/27 |
| POINT E | 92/3540 | 88/389 | 96/2955 |
| POINT F | 32/14 | 59/10 | 32/21 |
| POINT G | 41/14 | 74/6 | 34/20 |
| POINT H | 24/18 | 62/10 | 41/15 |
| POINT I | 35/19 | 58/6 | 29/21 |
| MEAN VALUE (%) | 39.0/406.8 | 67.3/49.9 | 43.8/350.0 |
| DEGREE OF VARIABILITY (%) | 53.2/288.8 | 14.1/254.9 | 48.0/279.1 |
| COMPARISON 2 | | | |
| POINT A | 24/21 | 55/10 | 28/20 |
| POINT B | 31/16 | 54/60 | 36/21 |
| POINT C | 27/17 | 66/11 | 33/24 |
| POINT D | 41/16 | 67/5 | 33/16 |
| POINT E | 26/2960 | 94/3 | 87/3750 |
| POINT F | 103/10 | 54/421 | 41/12 |
| POINT G | 21/12 | 69/7 | 28/11 |
| POINT H | 32/14 | 62/10 | 36/14 |
| POINT I | 31/16 | 70/14 | 28/23 |
| MEAN VALUE (%) | 37.3/342.4 | 65.7/54.1 | 38.9/432.3 |
| DEGREE OF VARIABILITY (%) | 67.7/286.6 | 18.9/254.3 | 47.8/287.8 |
| COMPARISON 3 | | | |
| POINT A | — | 63/3 | 33/17 |
| POINT B | — | 71/6 | 27/11 |
| POINT C | — | 54/10 | 35/21 |
| POINT D | — | 60/6 | 28/14 |
| POINT E | — | 103/411 | 82/4926 |
| POINT F | — | 71/10 | 40/16 |
| POINT G | — | 58/9 | 39/17 |
| POINT H | — | 64/5 | 28/21 |
| POINT I | — | 70/10 | 39/11 |
| MEAN VALUE (%) | — | 68.2/52.2 | 39.0/561.6 |
| DEGREE OF VARIABILITY (%) | — | 21.0/257.7 | 43.4/291.5 |

NOTE) THE EXPRESSIONS INCLUDING A SLASH MARK IN THE TABLE INDICATE (CONCENTRATION % IN THE WATER/CONCENTRATION % IN THE SURFACE LAYER OF THE SOIL).

As shown in Table 2 and Table 3, the uniformity of the component of water, and the uniformity of the concentration of the component of the surface layer of the soil in Examples 3, 4 and 8, are satisfactory, but in Comparisons 1 to 3, since a portion of the composition is precipitated on the bottom of the water, the concentration of the active component of the surface layer of the soil at the point of the scattering (application) is extremely high, which causes fears of phytotoxicity.

TEST EXAMPLE 3

Application of the Present Invention on a Rice Paddy Field

In mid-May, a rice plant (breed: sasanishiki) was transplanted on a paddy of 20 m×50 m in area, and 7 days later, 10 bags of the agricultural chemicals formulation for a rice paddy field obtained in Example 3 were thrown from a path between the paddy fields to be scattered nearly uniformly. It was observed that the water-soluble film was dissolved 8 minutes after the treatment, and the packed composition spread while floating on the water surface without precipitation on the bottom of the padding field. Incidentally, the wind blew at the velocity of 2 m to 4 m on the date of the treatment. On a paddy field in which no agricultural chemicals are scattered (applied), there observed weeds such as nobie, urikawa, Japanese parsley and matsubai, but on a paddy field in which the agricultural chemicals formulation for a rice paddy field of the present invention are scattered, growth of weeds can not be observed and symptom of ill effects by the chemicals is not observed.

The agricultural chemicals formulation of the present invention has an effect that the agricultural active ingredient is uniformly spread over the whole surface of the paddy field without increase of concentration of the agrochemical ingredient at the point of the treatment because floatability of the composition packed in a water-soluble film is excellent and the composition would not be precipitated on the bottom of the water.

What is claimed is:

1. An agricultural chemicals formulation for a rice paddy field, comprising a water-soluble film packing a granular composition, wherein the granular composition is formed by letting a granular nucleus hold and carry a mixture of a liquid agrochemically active ingredient at room temperature, a surfactant, and a substance exhibiting a thickening function or a gelation function in the water.

2. The agricultural chemicals formulation for a rice paddy field according to claim 1, wherein said substance exhibiting a thickening function or a gelation function in the water is held and carried by said granular nucleus in a state that said substance is not fixed on said granular nucleus firmly.

3. The agricultural chemicals formuation for the rice paddy field according to claim 1, wherein said liquid agrochemically active ingredient is an agrochemically active ingredient originally liquid at room temperature or a solid agrochemically active ingredient at room temperature which is dissolved or dispersed in a solvent.

4. The agricultural chemicals formuation for the rice paddy field according to claim 1, wherein said substance exhibiting a thickening function or a gelation function in the water is a water-soluble polymer exhibiting a thickening function.

5. The agricultural chemicals formation for the rice paddy field according to claim 1, wherein said granular nucleus has a shorter diameter of 0.1 to 10 mm and a bulk specific gravity of 1 or less.

6. The agricultural chemicals formuation for the rice paddy field according to claim 1, wherein said substance exhibiting a thickening function or a gelation function is a solid powdery substance.

7. The agricultural chemicals formuation for the rice paddy field according to claim 1, wherein said agricultural chemical formulation has a weight of 10 g to 200 g per one bag thereof.

8. A method of applying an agrochemically active ingredient for a rice paddy field, comprising the steps of;
    throwing directly the agricultural chemicals formuation for the rice paddy field according to claim 1 into the paddy field filled with water at a rate of 2 to 20 bags per 10 a.

9. A method of applying an agrochemically active ingredient in the agricultural chemicals formuation for the rice paddy field according to claim 1, wherein said agricultural chemicals formuation rice paddy field is thrown into a paddy filed filled with water, and the granular nucleus in the composition is temporarily bonded together under the influence of a substance exhibiting a thickening function or gelation function in the water, which attaches on the surface of the granular nucleus, so that at least the greater portion of said granular nucleus containing granular nucleus having a small buoyancy can be floated on the surface of water by the help of the granular nucleus having a large buoyancy, thereby spreading and scattering the active ingredients of the agricultural chemicals formuation for the rice paddy field.

10. The agricultural chemicals formulation for the rice paddy field according to claim 1, wherein said granular nucleus is at least one vegetable matter selected from the group consisting of rice hull, sugar cane, rice straw, wheat straw, coconut, banana, bamboo, reed, kenaf, corn nucleus, and wood.

11. A method for producing an agricultural chemicals formulation for a rice paddy field, comprising the steps of;

preparing a granular composition by letting a granular nucleus hold and carry a mixture of a liquid agrochemically active ingredient at room temperature, a surfactant, and a substance exhibiting a thickening function or a gelation function in the water; and packing said granular composition into a water-soluble film.

* * * * *

UNITED STATES PATENT AND TRADEMARK OFFICE
CERTIFICATE OF CORRECTION

PATENT NO.  : 6,486,095 B1
DATED       : November 26, 2002
INVENTOR(S) : Shigeki Fujita et al.

It is certified that error appears in the above-identified patent and that said Letters Patent is hereby corrected as shown below:

Column 3,
Line 56, "benthiocarb" should read -- thiobencarb --.

Column 4,
Line 27, "2methythio-4,6-bis(ethylamino)-s=" should read -- 2methythio-4,6-bis(ethylamino)-s- --.
Line 28, "simetiyne" should read -- simetryne --.
Line 35, "2-[4-(2,4=dichlorobenzoyl)-1," should read -- 2-[4-(2,4-dichlorobenzoyl)-1 --.
Line 38, "clomeprop)" should read -- (clomeprop) --.
Line 61, "urea25" should read -- urea --.

Column 5,
Line 7, "5(oxolinic" should read -- (oxolinic --.

Column 10,
Line 37, "benthiocarb" should read -- thiobencarb --.
Line 57, "benthiocarb" should read -- thiobencarb --.

Column 11,
Line 8, "benthiocarb" should read -- thiobencarb --.

Column 12,
Line 37, "benthiocarb" should read -- thiobencarb --.
Line 50, "benthiocarb" should read -- thiobencarb --.

UNITED STATES PATENT AND TRADEMARK OFFICE
CERTIFICATE OF CORRECTION

PATENT NO. : 6,486,095 B1
DATED : November 26, 2002
INVENTOR(S) : Shigeki Fujita et al.

It is certified that error appears in the above-identified patent and that said Letters Patent is hereby corrected as shown below:

Column 14,
Line 14, "BENTIOCARB" should read -- THIOBENCARB --.

Column 15,
Line 3, "BENTIOCARB" should read -- THIOBENCARB --.

Column 17,
Line 4, "rice paddy field" should read -- for the rice paddy field --.

Signed and Sealed this

Twenty-second Day of April, 2003

JAMES E. ROGAN
*Director of the United States Patent and Trademark Office*